United States Patent [19]

Krbechek

[11] 4,171,317

[45] Oct. 16, 1979

[54] SELECTIVE CONVERSION OF 20-METHYLPREGNA-3,5,20(21)-TRIENE-3,21-DIOL-DIACETATE TO 3-OXO-20-METHYLPREGNA-4,20(21)-DIENE-21-YL-ACETATE

[75] Inventor: LeRoy O. Krbechek, Golden Valley, Minn.

[73] Assignee: Henkel Corporation, Minneapolis, Minn.

[21] Appl. No.: 890,101

[22] Filed: Mar. 27, 1978

[51] Int. Cl.$^2$ ............................................. C07J 5/00
[52] U.S. Cl. ............................ 260/397.47; 260/397.3; 260/397.4
[58] Field of Search ................................ 260/397.47; /Machine Searched Steroids

[56] References Cited

U.S. PATENT DOCUMENTS

| | | | |
|---|---|---|---|
| 2,595,596 | 5/1952 | Moffett | 260/239.55 |
| 3,320,289 | 5/1967 | Fried et al. | 260/397.4 |

FOREIGN PATENT DOCUMENTS 1012794 12/1965 United Kingdom ................. 260/397.4

Primary Examiner—Ethel G. Love
Attorney, Agent, or Firm—Patrick J. Span; Elizabeth Tweedy; Forrest L. Collins

[57] ABSTRACT

The present invention relates to the conversion of 20-methylpregna-3,5,20(21)-triene-3,21-diol-diacetate to 3-oxo-20-methylpregna-4,20(21)-diene-21-yl-acetate through the use of a halogenated solvent and a halogenated acid. The benefits of the present invention include a substantial increase in the production of progesterone via ozonolysis technology.

20 Claims, No Drawings

SELECTIVE CONVERSION OF 20-METHYLPREGNA-3,5,20(21)-TRIENE-3,21-DIOL-DIACETATE TO 3-OXO-20-METHYLPREGNA-4,20(21)-DIENE-21-YL-ACETATE

BACKGROUND OF THE INVENTION

1. Field of the Invention

The present invention discusses increased recovery of intermediates which are useful for the preparation of sex hormones.

2. Discussion of the Art

It has long been known that many sex hormones may be prepared chemically through a variety of oxidation and reduction reactions. For instance, in an article entitled "Progesterone from 3-acetoxybisnor-5-cholenaldehyde and 3-ketobisnor-4-cholenaldehyde" by Heyl et al, June 1950, JACS; pp. 2617–2619, the aforementioned compounds are described as useful in the production of progesterone.

Basically the Heyl et al article, supra, discloses that the named subject compounds may be treated with acetic anhydride using sodium acetate as a catalyst to form the corresponding bisenol acetate and the 21 enol acetate. These compounds are then treated as discussed in the reference through chemical conversion to give progesterone.

In particular, one aspect of the Heyl et al reference discloses that by using stigmasterol as a starting material in an Oppenauer oxidation stigmastadienone is obtained. Through ozonolysis of the stigmastadienone a relatively high yield of 3-ketobisnor-4-cholenaldehyde may be obtained. The 3-ketobisnor-4-cholenaldehyde is then converted to the enol acetate and bisenol acetate through heating at reflux under nitrogen for six hours in a mixture of acetic anhydride and sodium acetate. The product of the acetic anhydride treatment which is described as a slightly yellow residue, is then dissolved in chloroform. Through this process the insoluble sodium acetate remaining in the reaction mixture may be filtered off and washed with additional chloroform to increase the recovery of the enol acetate and bisenol acetate products.

Both enol acetates are then described as being subjected to ozonolysis, followed by vacuum removal of the solvent. This residue comprising the ozonized product is then taken up in acetic acid and ether followed by mixing with zinc dust. This mixture is then stated as having been diluted with ether, filtered, and the ether solution washed with a sodium hydroxide solution, water and dried. The ether is then evaporated and the residue is refluxed with a mixture of methanol and sulfuric acid to hydrolize any C-3 enol ester which may be present in the ozonized mixture. The Heyl et al reference then goes on further to state that this latter solution may be concentrated by vacuum to half its volume and extracted with ether. The ether solution is then stated to be washed with sodium hydroxide, water and dried over sodium sulfate. Progesterone is stated to be obtained by taking the dried residue up in anhydrous ether through warming and then allowing the prisms of progesterone to separate on standing. The over-all yield of progesterone is stated to be 60%.

It has now been found that through following the process described in the Heyl et al reference, that a by-product is obtained which diminishes the potential yield of progesterone. Moreover, the by-products are extremely difficult to separate from progesterone due to the similar structure. The by-products are a mixture of 6-alpha and 6-beta hydroxy progesterones. The production of these 6-hydroxy progesterone compounds has been found to be proportional to the amount of bisenol acetate present in the mixture of enol acetate and bisenol acetate.

It is, therefore, desirable to minimize the amount of the bisenol acetate which is present with the enol acetate in order to greatly increase the amount of progesterone formation upon subsequent processing.

Throughout the specification and claims percentages and ratios are given by weight and temperatures are in degrees Celsius, unless otherwise indicated.

The use of the terms enol acetate and bisenol acetate herein correspond to 3-oxo-20-methylpregna-4,20(21)-diene-21-yl-acetate and 20-methylpregna-3,5,20(21)-triene-3,21-diol-diacetate respectively. It is also noted that 3-ketobisnor-4-cholenaldehyde referred to in Heyl et al is also known as 3-keto-4-pregnene-20-carboxaldehyde.

SUMMARY OF THE INVENTION

The present invention describes a process for the selective conversion of 20-methylpregna-3,5,20(21)-triene-3,21-diol-diacetate to 3-oxo-20-methylpregna-4,20(21)-diene-21-yl-acetate, including the steps of treating 20-methylpregna-3,5,20(21)-triene-3,21-diol-diacetate with a sufficient amount of a halogenated acid or mixtures thereof in the presence of a halogenated solvent or mixtures thereof until the formation of 3-oxo-20-methylpregna-4,20(21)-diene-21-yl-acetate from the 20-methylpregna-3,5,20(21)-triene-3,21-diol-diacetate is substantially complete.

DETAILED DESCRIPTION OF THE INVENTION

The present invention as previously noted, relates to a method for improving the yield of progesterone through the route described in the Heyl et al article, which is herein incorporated by reference. Through following the practice of the present invention it is possible to substantially increase the yield of progesterone over the procedure described in the reference. In carrying out the acetylation reaction of the reference to form the enol acetate and bisenol acetate, it has been found that the initial yield of the enol acetate will be from about 70 to 80% of that corresponding to the initial aldehyde. The bisenol acetate formed in the mixture with the enol acetate corresponds to approximately 20 to 30% of the starting aldehyde. The formulas show (I) the starting aldehyde; (II) the bisenol acetate; and (III) the enol acetate. Also shown below (IV) is the 6-alpha/6-beta hydroxy progesterone and (V) progesterone.

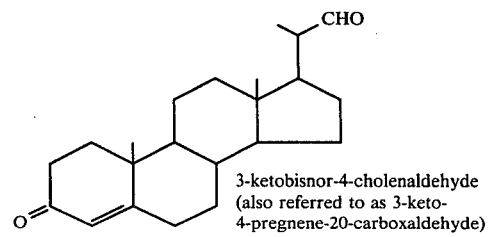

3-ketobisnor-4-cholenaldehyde (also referred to as 3-keto-4-pregnene-20-carboxaldehyde)

I

-continued

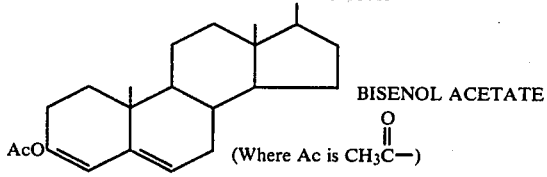

BISENOL ACETATE (Where Ac is CH₃C(=O)—)

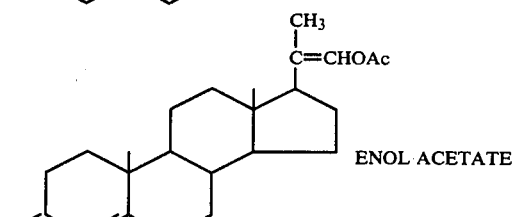

ENOL ACETATE

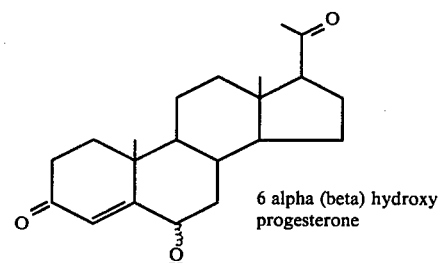

6 alpha (beta) hydroxy progesterone

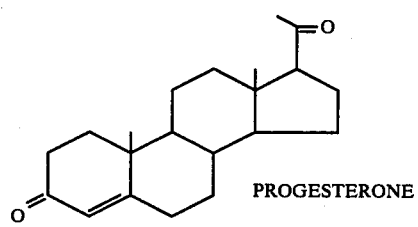

PROGESTERONE

In carrying out the selective conversion of the bisenol acetate to the enol acetate it has been found that serious problems are encountered. Specifically, it is first necessary to obtain the requisite conditions such that only the 3-acetoxy group is deacetylated leaving the 21-acetoxy group intact.

The foregoing point on not disturbing the 21-acetoxy structure is important in that the preferred aspect of the present invention involves treating a mixture of the enol acetate and the bisenol acetate without first separating the compounds. While the invention may be utilized to convert a substantially pure mixture of the bisenol acetate to the enol acetate the invention is not so limited. Where a mixture of the bisenol acetate and the enol acetate is used the respective weight ratio should be from about 15:1 to about 1:40, preferably from about 5:1 to about 1:30.

It has first been found that halogenated acids of considerable acid strength may be used to accomplish the deacetylation. Other strong acids such as oxalic acid and para-toluene-sulfonic acid when used to replace the halogenated acids did not result in substantial conversion to the desired enol acetate.

Secondly, in view of the fact that a strong proton donating acid is needed to convert the bisenol acetate to the enol acetate it becomes necessary to select a suitable solvent system for accomplishing this organic reaction. As mentioned above, oxalic and para-toleunesulfonic acids which are extremely strong proton donors have been found to be unsuitable in the 3-acetoxy deacetylation reaction when compared to the halogenated acids.

It is observed that the present invention utilizes not only a strong proton donating halogenated acid, but also a suitable halogenated solvent such as are later described. That is, it has been found that the mixture of the enol acetate and bisenol acetate is substantially insoluble in water. While, of course, the mixture of the two enol acetates could be diluted to infinity in an aqueous solution followed by 3-acetoxy deacetylation; such would not be economical in considering that the solvent must be eventually removed from the reaction mixture in order to concentrate the desired end product.

Thus, in the present invention, it has been found first that deacetylation of the three acetoxy structure of the bisenol acetate is effected by a halogenated acid; and secondly, that by using a halogenated solvent the reaction proceeds quite rapidly with almost total conversion to the desired enol acetate.

Suitable solvents for use in the present invention include any commonly available halogenated solvent. Most preferably, of course, the halogenated solvent will be a liquid at the operating temperatures of the reaction to avoid undue use of pressurizing equipment. The degree of halogenation of the solvent is not particularly critical. It has been found, however, that the preferred solvents for use in converting the bisenol acetate to the enol acetate are chlorinated solvents. Suitable examples of halogenated solvents useful in the present invention include: methylene chloride, chloroform, ethylene dichloride, methylene bromide, 2-chloroethanol and carbon tetrachloride. The preferred solvent for conducting the reaction of the present invention is methylene chloride.

If desired, these solvents may be used in mixture with one another. A particularly preferred system is the use of 2-chloroethanol in mixture with methylene chloride. Mixtures of the halogenated solvents are conveniently employed at from about 20:1 to about 1:2, more preferably about 15:1 to about 2:1 by volume.

With respect to choosing the acid for the 3 acetoxy deacetylation it is again noted that oxalic and para-toluenesulfonic acids were found unsuitable. This unsuitability of aqueous solutions of the foregoing acids is believed to be due to a lack of solubility in the organic system. It is, therefore noted, that some halogenated acids which may be used in the present invention are not preferred due to their ability to strongly oxidize as well as to deacetylate. The most common halogenated acids useable herein include hydrochloric, halogenated acetic acids such as trichloroacetic acid, and trifluoroacetic acid, trifluoromethanesulfonic acid, hydrobromic acid, hydrofluoric acid, and hydroiodic acid.

It is also noted, for some unexplained reason, that the location of the halogen portion of the halogenated acid is apparently unimportant to the success of utilizing the acid in the deacetylation reaction. That is, trichloroacetic acid where the chlorine molecules are covalently bonded to a carbon atom is utilizable as is hydrochloric acid which presents the halogen as an ion.

Of the aforementioned acids, hydroiodic acid which may be used is perhaps the least suitable of the halogenated acids due to its oxidizing properties. Concentrated aqueous hydrochloric acid is preferred due to its high acid strength and suitable solubility in the halogenated solvents. A preferred combination of halogenated solvent and halogenated acid is methylene chloride and hydrochloric acid. The system may be further improved by the addition of short chain aliphatic acids such as acetic acid, preferably glacial acetic acid as a cosolvent. Further improvement may be obtained by utilizing dioxane as a cosolvent with the halogenated solvent. The cosolvent is conveniently used in a volume ratio to the halogenated acid of from about 20:1 to about 1:2, preferably from about 15:1 to about 2:1.

In most practical aspects of the present invention it is desirable to use the halogenated acid in as concentrated a form as possible to maximize the 3-acetoxy deacetylation of the bisenol acetate.

Stated otherwise the halogenated acid is recognized as being solvated in a sufficient amount of water or an alcohol such as methanol, ethanol or isopropanol to effect freeing of the proton in the halogenated solvent.

Typical methods of measuring the strength of the acid utilized are, of course, unsuitable due to the fact that the reaction mixture is substantially non-aqueous. That is, pH only has meaning in aqueous solutions. In an attempt to quantify the amount of hydrogen ions necessary to accomplish the deacetylation it is suggested that the weight ratio of the acidic hydrogen concentration of the halogenated acid to the halogenated solvent should be from about $10^{-1}:1$ to about $10^{-6}:1$. That is, the weight ratio represents the available protons in the acid, which would be available if the acid were dissolved in water. This weight ratio of the acidic hydrogen concentration of the halogenated acid to the halogenated solvent is preferably from about $10^{-3}:1$ to about $10^{-5}:1$.

The amount of the halogenated solvent utilized in the deacetylation is any convenient amount preferably in a weight ratio to the bisenol acetate at from about 500:1 to about 1:1, most preferably from about 100:1 to about 2:1.

It has also been found in conducting the present invention, that following the conversion of the bisenol acetate to the enol acetate, that an aqueous wash of the reaction mixture provides still higher yields of progesterone following ozonolysis than if the halogenated acid is not so washed out. It has further been found that an alkaline wash with a material such as sodium hydroxide following the initial aqueous wash gives still greater progesterone conversion. That is, while an alkaline wash may be used first even better results are obtained where the first aqueous wash is neutral. These results, as previously noted, are unexplained but nonetheless beneficial in increasing the yield of progesterone.

One final parameter to be discussed in the conversion of the bisenol acetate to the enol acetate is that of the maintenance of the temperature during the conversion. It will be observed that the reaction itself may take place over a wide temperature range which is conveniently maintained between about $-20$ degrees C. to about 50 degrees C., preferably the reaction temperature is maintained between $-5$ degrees C. and $+10$ degrees C.

The following exemplifies the present invention:

EXAMPLE I

A mixture of the bisenol acetate and the enol acetate is obtained having an analysis showing less than 0.1% of the starting aldehyde, 38% of the enol acetate and approximately 60% of the bisenol acetate.

The mixture of the bisenol acetate and the enol acetate weighing 480 grams is dissolved in 1.5 liters of methylene chloride and filtered free of inorganic salts. It is noted that potassium acetate is used as a catalyst in the reference procedure for manufacturing the enol acetate mixture thus accounting for the salt in the mixture. The inorganic residue is then washed with an additional quantity of about 0.5 liter methylene chloride such that the total methylene chloride filtrates equal about 2 liters.

The methylene chloride and the mixture of the bisenol acetate and enol acetate is maintained under constant stirring at 3 degrees C. for ten hours in the presence of 20 milliliters of concentrated hydrochloric acid (13.1 molar in water).

At the end of the ten hour period the mixture was successively washed with 1 liter of water, 1 liter of a 2% sodium hydroxide solution, and an additional 1 liter of water before drying over calcium sulfate. The calcium sulfate is then removed by filtration and washed with additional methylene chloride thereafter combining the filtrates. The methylene chloride is then removed at reduced pressure leaving 372 grams of solid residue. A gas chromatograph analysis of a sample of the residue shows 1.4% of the starting aldehyde and 85.1% of the enol acetate. No bisenol acetate was reported.

Substantially similar results may be obtained by substituting chloroform, ethylene dichloride, 2-chloroethanol, methylene bromide or carbon tetrachloride for the methylene chloride solvent. Moreover, similar conversion yields are observed upon substituting aqueous solutions of trichloroacetic acid, trifluoroacetic acid, trifluoromethanesulfonic acid, hydrobromic acid, hydrofluoric acid or hydroiodic acid, for the hydrochloric acid.

An overall increase in the rate of enol acetate formation is found by utilizing 2-chloroethanol or glacial acetic acid in a ten fold (V/V) excess over the hydrochloric acid in the above example.

Thus, the present invention accomplishes the goal of converting the bisenol acetate to the enol acetate thereby minimizing the presence of by-products which diminish the overall yield of progesterone.

What is claimed is:

1. A process for the selective conversion of 20-methylpregna-3,5,20(21)-triene-3,21-diol-diacetate to 3-oxo-20-methylpregna-4,20(21)-diene-21-yl-acetate, including the steps of treating 20-methylpregna-3,5,20(21)-triene-3,21-dioldiacetate with a sufficient amount of a halogenated acid or mixtures thereof in the presence of a halogenated solvent or mixtures thereof until the formation of 3-oxo-20-methylpregna-4,20(21)-diene-21-yl-acetate from the 20-methylpregna-3,5,20(21)-triene-3,21-diol-diacetate is substantially complete.

2. The process of claim 1 wherein a mixture of 20-methylpregna-3,5,20(21)-triene-3,21-diol-diacetate and 3-oxo-20-methylpregna-4,20(21)-diene-21-yl-acetate are present prior to the conversion.

3. The process of claim 2 wherein the weight ratio of 20-methylpregna-3,5,20(21)-triene-3,21-diol-diacetate to 3-oxo-20-methylpregna-4,20(21)-diene-21-yl-acetate in the mixture is from about 15:1 to about 1:40.

4. The process of claim 1 wherein the solvent is present in a weight ratio to the 20-methylpregna-3,5,20(21)-triene-3,21-diol-diacetate from about 500:1 to about 1:1 by weight.

5. The process of claim 1 wherein the weight ratio of the acidic hydrogen concentration of the halogenated acid to the halogenated solvent is from about $10^{-1}:1$ to about $10^{-6}:1$.

6. The process of claim 1 wherein the halogenated solvent is a chlorinated solvent.

7. The process of claim 1 wherein the halogenated acid is selected from the group consisting of hydrochloric acid, trichloroacetic acid, trifluoroacetic acid, trifluoromethanesulfonic acid, hydrobromic acid, hydrofluoric acid, and hydroiodic acid and mixtures thereof.

8. The process of claim 1 including an aqueous wash step following the conversion.

9. The process of claim 1 including an alkaline wash step following conversion.

10. The process of claim 1 wherein an aqueous wash step and an alkaline wash step are successively performed following the conversion of 20-methylpregna-3,5,20(21)-triene-3,21-diol-diacetate to the 3-oxo-20-methylpregna-4,20-(21)-diene-21-yl-acetate.

11. The process of claim 10 wherein the temperature during conversion of the 3,21-diol-diacetate to the 3-oxo-20-methylpregna-4,20(21)-diene-21-yl-acetate is maintained between about −20 degrees C. to about 50 degrees C.

12. The process of claim 1 wherein the halogenated solvent is selected from the group consisting of methylene chloride, chloroform, ethylene dichloride, methylene bromide, 2-chloroethanol and carbon tetrachloride and mixtures thereof.

13. The process of claim 1 wherein the halogenated solvent is methylene chloride.

14. The process of claim 1 wherein the halogenated acid is hydrochloric acid.

15. The process of claim 1 wherein the chlorinated solvent is methylene chloride and the halogenated acid is hydrochloric acid.

16. The process of claim 1 wherein a mixture of halogenated solvents is used in a volume ratio of from about 20:1 to about 1:2.

17. The process of claim 16 wherein the mixture of halogenated solvents includes methylene chloride and 2-chloroethanol.

18. The process of claim 1 wherein a cosolvent selected from the group consisting of short chain aliphatic acids is employed.

19. The process of claim 18 wherein the cosolvent is acetic acid.

20. The process of claim 19 wherein the cosolvent is glacial acetic acid.

* * * * *